(12) United States Patent
Poulter et al.

(10) Patent No.: US 10,556,853 B2
(45) Date of Patent: Feb. 11, 2020

(54) ANTICONVULSANT COMPOUNDS

(71) Applicant: OWEN-BARRY PHARMACEUTICALS INC., London (CA)

(72) Inventors: Michael Poulter, London (CA); Tony Durst, Ottawa (CA)

(73) Assignee: OWEN-BARRY PHARMACEUTICALS INC., London (CA)

( * ) Notice: Subject to any disclaimer, the term of this patent is extended or adjusted under 35 U.S.C. 154(b) by 0 days.

(21) Appl. No.: 15/866,924

(22) Filed: Jan. 10, 2018

(65) Prior Publication Data

US 2018/0194715 A1 Jul. 12, 2018

Related U.S. Application Data

(60) Provisional application No. 62/444,474, filed on Jan. 10, 2017.

(51) Int. Cl.

| C07C 69/78 | (2006.01) |
|---|---|
| C07C 65/32 | (2006.01) |
| C07C 49/753 | (2006.01) |
| C07C 49/697 | (2006.01) |
| C07C 49/683 | (2006.01) |
| C07C 235/84 | (2006.01) |
| C07C 317/24 | (2006.01) |
| C07C 321/28 | (2006.01) |
| C07C 255/40 | (2006.01) |
| C07C 49/603 | (2006.01) |
| C07D 211/08 | (2006.01) |
| A61P 25/08 | (2006.01) |

(52) U.S. Cl.
CPC .............. *C07C 69/78* (2013.01); *A61P 25/08* (2018.01); *C07C 49/603* (2013.01); *C07C 49/683* (2013.01); *C07C 49/697* (2013.01); *C07C 49/753* (2013.01); *C07C 65/32* (2013.01); *C07C 235/84* (2013.01); *C07C 255/40* (2013.01); *C07C 317/24* (2013.01); *C07C 321/28* (2013.01); *C07D 211/08* (2013.01)

(58) Field of Classification Search
CPC .... A61K 31/00; A61K 31/122; C07C 235/84; C07C 255/40; C07C 317/24; C07C 321/28; C07C 49/603; C07C 49/623; C07C 49/67; C07C 49/683; C07C 49/697; C07C 49/723; C07C 49/753; C07C 63/66; C07C 65/32; C07C 69/157; C07C 69/76; C07C 69/78; C07D 211/08; C07D 295/192; A61P 25/08; A61P 25/10; A61P 25/12

See application file for complete search history.

(56) References Cited

U.S. PATENT DOCUMENTS

| 3,820,975 A | 6/1974 | Poje et al. |
|---|---|---|
| 4,391,827 A * | 7/1983 | Harbert ............ C07C 37/055 514/125 |
| 7,399,888 B2 | 7/2008 | Rahman et al. |
| 2014/0221682 A1 | 8/2014 | Rahman et al. |
| 2015/0148417 A1 | 5/2015 | Rahman et al. |

FOREIGN PATENT DOCUMENTS

| GB | 2226555 A | 7/1990 |
|---|---|---|
| KR | 2016120989 A | 10/2016 |
| WO | 9901416 A2 | 1/1999 |
| WO | 03040084 A1 | 5/2003 |
| WO | 2011034832 A1 | 3/2011 |

OTHER PUBLICATIONS

Wagle et. al., European Journal of Medicinal Chemistry, 2009, Elsevier, vol. 44, pp. 1135-1143 (Year: 2009).*
Dikova, Anna, et al. Advanced Synthesis & Catalysis (2015), 357(18), 4093-4100.
Cheval, Nicolas, et al. Chemistry—A European Journal (2013), 19(27), 8765-8768.
Khalaf, Juhienah, et al. ACS Combinatorial Science (2011), 13(4), 351-356.
Azzaro, Marcel, et al. Journal of Chemical Research, Synopses (1979), (4), 134-5.
Walker, Sarah E., et al. Organic Letters (2013), 15(8), 1886-1889.
Liang, Yu-Feng, et al. Green Chemistry (2016), 18(24), 6462-6467.
Fall, Yacoub, et al. Tetrahedron (2009), 65(2), 489-495.
Cahiez, Gerard, et al. Tetrahedron Letters (1998), 39(34), 6159-6162.
Geribaldi, Serge, et al. Journal of the Chemical Society, Perkin Transactions 2: Physical Organic Chemistry (1972-1999) (1986), (8), 1327-30.
Yang, Shyh-Ming, et al. Journal of Organic Chemistry (2016), 81(8), 3464-3469.
Cahiez, Gerard, et al. Chemistry—A European Journal (2012), 18(19), 5860-5863, S5860/1-S5860/45.
Liu, Xiaoguang, et al. Organic Letters (2015), 17(14), 3572-3575.
Kumari, Kumkum, et al. Synlett (2014), 25(2), 213-216.
Thakur, Ashish, et al. Chemical Communications (Cambridge, United Kingdom) (2012), 48(2), 203-205.
Liu, X. et al. "Copper-Catalyzed y-Sulfonylation of a,β-Unsaturated Carbonyl Compounds by Means of Silyl Dienol Ethers", Org. Lett., Jul. 1, 2015 (Jul. 1, 2015), vol. 17, pp. 3572-3575.
Azzaro, Marcel, et al. Journal of Organic Chemistry (1982), 47(25), 4981-4.
Danishefsky, S. et al. "On the Use of β-Phenylsulfinyl-a,β-Unsaturated Carbonyl Dienophiles in Diels-Alder Reactions", J. Am. Chem. Soc., Nov. 7, 1979 (Nov. 7, 1979), vol. 101 (23), pp. 7008-7012.

* cited by examiner

*Primary Examiner* — Sarah Pihonak
(74) *Attorney, Agent, or Firm* — Adler Pollock & Sheehan P.C.; Michel Morency

(57) ABSTRACT

The present application relates to compounds and methods for reducing the severity of convulsant activity or epileptic seizures, or for the treatment of chronic or acute pain.

20 Claims, 6 Drawing Sheets

ANTICONVULSANT COMPOUNDS

FIELD OF THE INVENTION

The present invention relates to compounds with anti-convulsant and pain activity. These compounds are useful in modulating voltage-gated sodium channel activity and are thus useful in the treatment of epilepsy and chronic or acute pain.

BACKGROUND

Anti-convulsant compounds are presently in wide use in the treatment of a variety of conditions and diseases, including epilepsy. Epilepsy is a neurological condition which affects the nervous system and causes affected individuals to suffer from seizures. These seizures are caused by in appropriate electrical communication between neurons in the brain and can be conceptualized as brain activity that is inappropriately synchronous. Seizures are often seen in electro encephalograms (EEGs) as high amplitude neural discharges that occur across brain regions. This brain activity is accompanied by behavioral disturbances that include loss of balance, jerking muscle movement, visual disturbances, and loss of consciousness. It is estimated that about 0.5% of the world's population has some form of epilepsy. Epilepsy is a lifelong condition, has a very low reversion rate, and is only rarely fatal. Persons with uncontrolled epilepsy are often under or un-employed.

The combination of all these factors makes epilepsy among the most expensive health care burdens in the world. In North America alone, the cost of epilepsy due to direct health care costs and lost economic activity is estimated to be in the billions of dollars each year. There is no known cure for epilepsy.

The control of epileptic seizures is an unmet medical challenge. Current medications control seizures by targeting a number of sites in the central nervous system (CNS). These drugs, while effective, often produce undesirable side effects that reduce compliance and therefor efficacy. Reportedly, nearly 30% of individuals with epilepsy do not respond to any current therapies, including both drug and brain stimulation therapies. Accordingly, there is a need to develop novel anticonvulsants in order to provide effective alternatives for these individuals.

As well the management of acute and chronic pain is an ongoing problem. There are millions of people living with various forms of chronic pain. Blocking sodium channel function is one of many treatments.

SUMMARY OF THE INVENTION

In one embodiment, the present invention relates to a method for eliminating or reducing the severity of convulsant activity or epileptic seizures by administering to a subject a therapeutically effective amount of a compound represented by the formula (I).

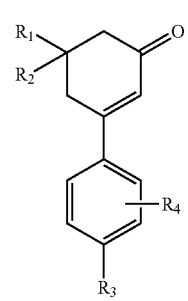

(I)

Where $R_1=R_2=CH_3$ or $R_1=H$ and $R_2=$aryl, wherein aryl is a compound selected from the group consisting of:
  phenyl, unsubstituted or substituted with one or two compounds selected from the group consisting of $CH_3$, OH, $OCH_3$, $SO_2CH_3$, $SO_2Ph$, F, Cl, $CF_3$, CN;
  1- or 2-naphthyl;
  2-, 3-, or 4-pyridyl, unsubstituted or substituted with one or two compounds selected from the group consisting of $CH_3$, $OCH_3$, $SO_2CH_3$, $SO_2Ph$, F, Cl, $CF_3$, CN;
  2- or 3-furyl, unsubstituted or substituted with one or two compounds selected from the group consisting of $CH_3$, $OCH_3$, $SO_2CH_3$, $SO_2Ph$, F, Cl, $CF_3$, CN; or
  2- or 3-thienyl, unsubstituted or substituted with one or two compounds selected from the group consisting of $CH_3$, $OCH_3$, $SO_2CH_3$, $SO_2Ph$, F, Cl, $CF_3$, CN;
$R_3=$H;
  $C(O)R_5$, wherein $R_5=$H, $CH_3$, $C_2H_5$, $CH(CH_3)_2$, $CHCH_3CN$, or aryl;
  $C(O)$—O—$R_6$, wherein $R_6=$pharmaceutically acceptable salts, H, C1 to C6 alkyl (straight chain or branched), $CH_2C_6H_5$, or $CH(CH_2)n$, and wherein n=2-5;
  $C(O)NH_2$, $C(O)NHR_6$ or $C(O)NR_7R_8$ wherein $R_7$ and $R_8$ independently=C1 to C6 alkyl (straight chain or branched), $CH_2C_6H_5$, aryl, or $R_7$ and $R_8$ together= $(CH_2)n$, and wherein n=3-5;
  OH, $OCH_3$, or $OCH_2C_6H_5$;
  S—$CH_3$, S—$C_6H_5$, $S(O)CH_3$, $S(O)C_6H_5$, $SO_2CH_3$, or $SO_2C_6H_5$;
  $NO_2$, $NH_2$, $NHR_6$, $NR_7R_8$, or pharmaceutically acceptable salts thereof; or
  C≡C—$C(O)CH_3$, C≡C—$C(O)CH(CH_3)_2$, C≡C—$C(O)C_2H_5$, C≡C—$C(O)C_6H_5$, C≡C—$C(O)$—OH, or pharmaceutically acceptable salts of C≡C—$C(O)$—$O^-$; or
  CN; and
$R_4=$one or two compounds selected from the group consisting of H, $CH_3$, OH, $OCH_3$, $SO_2CH_3$, $SO_2Ph$, F, Cl, $CF_3$, or CN In another embodiment, the method comprises administering to a subject a therapeutically effective amount of a compound represented by the following chemical formula.

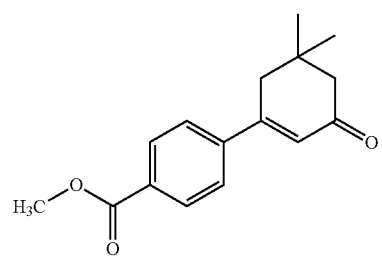 [SMILES: COC(=O)c1ccc(C2=CC(=O)CC(C)(C)C2)cc1]

In yet another embodiment, the present invention relates to a method for eliminating or reducing the severity of convulsant activity or epileptic seizures by administering to a subject a therapeutically effective amount of a compound represented by the formula (II).

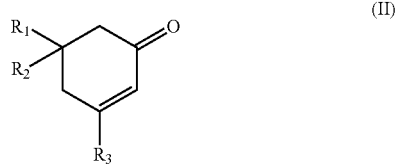

Where $R_1=R_2=CH_3$ or $R_1=H$ and $R_2=$aryl; and
$R_3=$C1 to C6 alkyl (straight chain or branched), $CH(CH_2)n$, wherein n=3-5, or aryl;
  $CH_2SC_6H_5$, or $CH_2SO_2C_6H_5$;
  $S-C_6H_5$, $S(O)C_6H_5$, or $SO_2C_6H_5$;
  $CH=CHC(O)CH_3$, $CH=CHC(O)C_6H_5$, $CH=CHC(O)-O-CH_3$, $CH=CHC(O)-O-C_2H_5$, $CH=CHC(O)-O-CH(CH_3)_2$, $CH=CHC(O)-O-C_4H_9$, or $CH=CHC(O)-O-C_6H_5$;
  $CH=CHCN$; or
  $CH=CHSO_2CH_3$, $CH=CHSO_2C_6H_5$.

In another aspect, the present invention relates to a pharmaceutical composition including a compound represented by the formula (I), or a pharmaceutically acceptable salt or solvate thereof, together with a pharmaceutically acceptable excipient.

In another embodiment, the composition includes a compound represented by the following chemical formula.

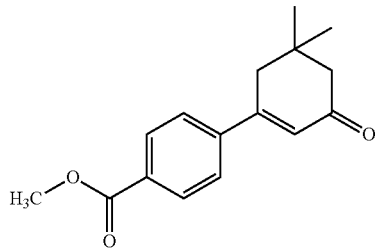

In yet another embodiment, the present invention relates to a pharmaceutical composition including a compound represented by the formula (II), or a pharmaceutically acceptable salt or solvate thereof, together with a pharmaceutically acceptable excipient.

BRIEF DESCRIPTION OF THE DRAWINGS

In order that the invention may be more clearly understood, preferred embodiments thereof will now be described in detail by way of example, with reference to the accompanying drawings, in which.

DESCRIPTION OF THE PREFERRED EMBODIMENTS

Figure 1:
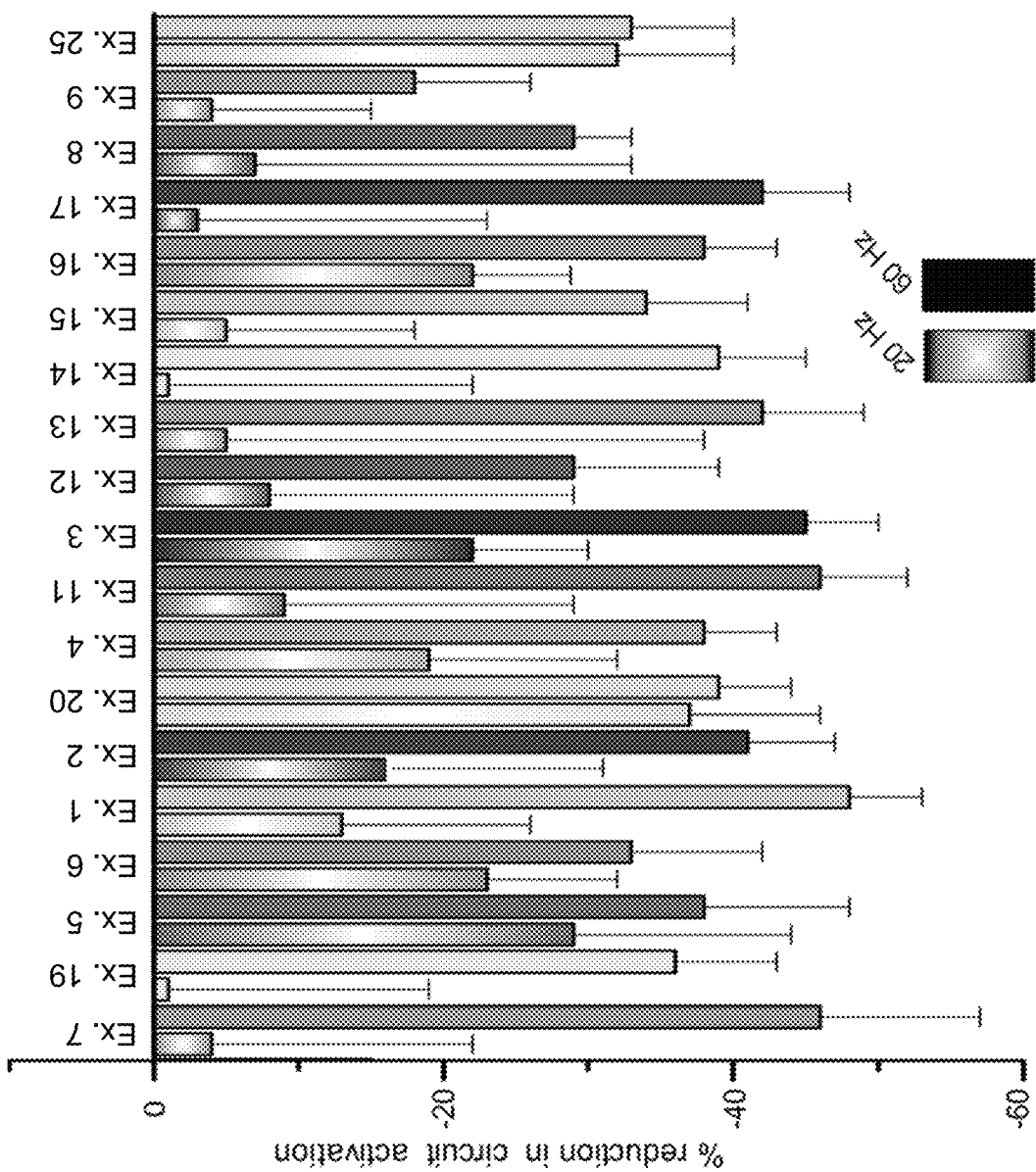
FIG. 1 is a graph showing a reduction in circuit activation for certain example compounds, according to the present invention.

It has been found that certain compounds, described herein, are voltage-gated sodium channel inhibitors with anti-convulsive activity. Voltage-gated sodium channels are found in the neurons of the central and peripheral nervous system and are responsible for generating the rapid upstroke of the action potential. They are essential to the nervous system's ability to initiate and propagate electrical signals.

The compounds represented by formula (I) and formula (II) are inhibitors of voltage-gated sodium channel activity and are useful in the treatment of epileptic seizures and pain. Preferred compounds of the invention are those listed in the Examples below and the pharmaceutically acceptable salts and solvates thereof.

Epileptic seizures are caused by disturbances in the electrical activity of the brain. In particular, excessive electrical brain activity is a hallmark of an epileptic seizure. The electrical activity of the brain is primarily mediated by voltage-gated sodium channels. Thus, the dampening of voltage-gated sodium channel activity is a common target to control epileptic disturbances.

The present invention also provides a method for eliminating or reducing the severity of convulsant activity or epileptic seizures by administering to a subject a therapeutically effective amount of a compound of formula (I) or (II), or a pharmaceutically acceptable salt or solvate thereof, together with a pharmaceutically acceptable excipient.

The present invention further provides a method for prophylactic treatment or prevention of epileptogenesis caused by traumatic brain injury by administering to a subject a therapeutically effective amount of a compound of formula (I) or (II), or a pharmaceutically acceptable salt or solvate thereof, together with a pharmaceutically acceptable excipient.

The compounds of the present invention may be administered orally, parenterally, or topically. Topical administration is preferred for treatment of pain.

The compounds of the present invention may be prepared by the procedures described below. According to a first procedure, a preferred compound of formula (I) may be prepared according to the following methodology, as illustrated by the general reaction sequences shown below:

General Procedure A

In this sequence a cyclic 1,3-diketone such as dimedone is converted in situ into its p-toluenesulfonate ester by reaction with p-toluenesulfonyl chloride in the presence of potassium carbonate in a dioxane-water mixture. To the reaction mixture thus obtained are added an arylboronic acid and a catalytic amount of tetrakis(triphenylphosphine)palladium(0). The resulting mixture is heated under reflux for 2 hours or until completion of the reaction, as monitored by analytical thin layer chromatography. Upon completion of the reaction, the mixture is extracted with EtOAc (3×10 mL), the combined organic extracts are dried with MgSO4, filtered and the solvent is evaporated via rotary evaporator. The product is isolated via column chromatography and characterized by 1H and 13C NMR and at times also by High Resolution Mass Spectrometry (HRMS).

Scheme A

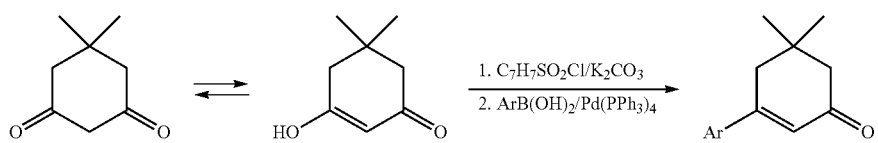

EXAMPLE 1

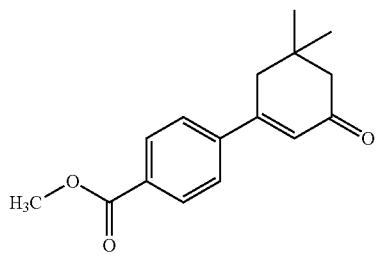 [SMILES: COC(=O)c1ccc(C2=CC(=O)CC(C)(C)C2)cc1]

pToluenesulfonyl chloride (1.65 g, 8.67 mmol) was added to a mixture of dimedone (935 mg, 6.67 mmol) and potassium carbonate (2.31 g, 16.7 mmol) in a 2:1 ratio of 1,4-dioxane (16 mL) and water (8 mL). This mixture was stirred at room temperature for 2 hours. 4-Methoxycarbonylphenylboronic acid (1.35 g, 8.56 mmol) and tetrakis(triphenylphosphine)-palladium(0) (231 mg, 0.20 mmol) were added and the mixture was heated under reflux for 4 hours. The resulting reaction mixture was extracted with EtOAc (3×10 mL). The extract was dried with MgSO$_4$, filtered and evaporate via rotary evaporator. The compound of example 1 was isolated via column chromatography and subsequent crystallization from 9:1 (diethyl ether:hexanes) as light-yellow crystals. Yield: 0.71 g, 41%.

$^1$H NMR (400 MHz, CDCl$_3$) δ, ppm: 8.09-8.00 (m, 2H), 7.63-7.48 (m, 2H), 6.44 (t, J=1.40 Hz, 1H), 3.93 (s, 3H), 2.66 (d, J=1.40 Hz, 2H), 2.36 (s, 2H), 1.14 (s, 6H). $^{13}$C NMR (100 MHz, CDCl$_3$) δ, ppm: 199.77, 166.42, 156.23, 143.42, 131.14, 129.93 (2C), 126.10 (2C), 125.72, 52.27, 50.90, 42.27, 33.79, 28.35 (2C)

HRMS. Calculated for C$_{16}$ H$_{18}$O$_3$: 258.1256. Found: 258.1233.

EXAMPLE 2

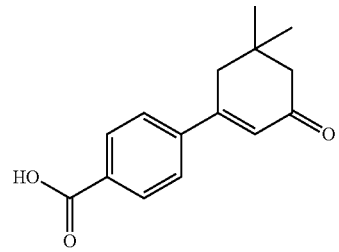

Methyl 3',3'-dimethyl-5'-oxo-2',3',4',5'-tetrahydro-[1,1'-biphenyl]-4-carboxylate (Compound 1) (50 mg, 0.19 mmol) was dissolved in methanol (4 mL) and a 5% sodium hydroxide aqueous solution was added (1 mL). This mixture was stirred at room temperature until disappearance of starting material was observed by TLC. Approximately one half of the methanol solvent was evaporated using a rotary evaporator and water (5 mL) was added. The mixture was extracted with EtOAc (3×5 mL) and the organic extract was discarded. The aqueous phase was treated with 5% hydrochloric acid aqueous solution (1 mL) and the mixture was extracted with EtOAc (3×5 mL). This second organic phase was dried with MgSO$_4$, filtered and evaporated to obtain the compound of example 2 as a white solid. (40 mg, 86%).

$^1$H NMR (400 MHz, CDCl$_3$) δ, ppm: 8.15 (d, J=8.49 Hz, 2H), 7.62 (d, J=8.51 Hz, 2H), 6.47 (t, J=1.31 Hz, 1H), 2.67 (d, J=1.31 Hz, 2H), 2.38 (s, 2H), 1.15 (s, 6H). $^{13}$C NMR (100 MHz, MeOH-D$_4$) δ, ppm: 201.15, 167.71, 158.33, 143.32, 131.82, 129.76 (2C), 126.08 (2C), 124.63, 50.29, 41.69, 33.33, 27.02 (2C)

HRMS. Calculated for C$_{15}$ H$_{16}$ O$_3$: 244.1099. Found: 244.1095.

EXAMPLE 3

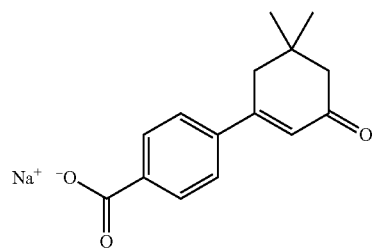

3',3'-dimethyl-5'-oxo-2',3',4',5'-tetrahydro-[1,1'-biphenyl]-4-carboxylic acid (Compound 1) (0.1 g, 0.41 mmol)

was dissolved in dichloromethane (10 mL) at room temperature. Sodium bis(trimethylsilyl)amide 1M (0.41 mL, 0.41 mmol) was added dropwise and a white precipitate was immediately observed. All the solvent was evaporated using a rotary evaporator and diethyl ether (10 mL) was added to the mixture. The sodium salt compound of example 3 was obtained as a fine beige powder after filtering the suspension. (96.5 mg, 88%)

$^1$H NMR (400 MHz, MeOH-D$_4$) δ, ppm: 7.97 (d, J=8.19 Hz, 2H), 7.60 (d, J=8.20 Hz, 2H), 6.39 (s, 1H), 2.73 (s, 2H), 2.33 (s, 2H), 1.11 (s, 6H). $^{13}$C NMR (100 MHz, MeOH-D$_4$) δ, ppm: 202.85, 174.01, 160.76, 142.17, 140.15, 130.77 (2C), 126.96 (2C), 125.14, 51.76, 43.20, 34.75, 28.48 (2C)

EXAMPLE 4

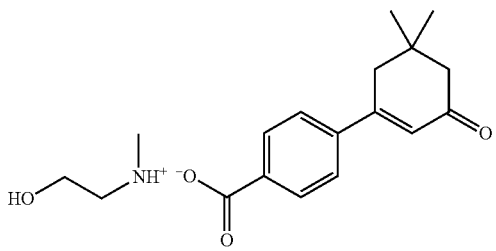

4

3',3'-dimethyl-5'-oxo-2',3',4',5'-tetrahydro-[1,1'-biphenyl]-4-carboxylic acid (Compound 1) (100 mg, 0.41 mmol) was dissolved in dichloromethane (10 mL). A solution of 2-dimethylaminoethanol (36.5 mg, 0.41 mmol) in 1 mL dichloromethane was added and the mixture was stirred for 10 minutes. The solvent was completely evaporated and diethyl ether (10 mL) was added to the mixture. The observed precipitated salt was filtered to obtain the ammonium salt compound of example 4 as a fine white powder. (103 mg, 75%)

$^1$H NMR (400 MHz, CDCl$_3$) δ, ppm: 8.08 (d, J=8.41 Hz, 2H), 7.55 (d, J=8.40 Hz, 2H), 6.44 (t, J=1.23 Hz, 1H), 4.00-3.91 (m, 2H), 3.12-3.05 (m, 2H), 2.80 (s, 6H), 2.67 (d, J=1.32 Hz, 2H), 2.35 (s, 2H), 1.14 (s, 6H). $^{13}$C NMR (100 MHz, MeOH-D$_4$) δ, ppm: 202.82, 173.85, 160.69, 142.34, 139.77, 130.79 (2C), 127.00 (2C), 125.20, 60.65, 57.08, 51.76, 43.88 (2C), 43.20, 34.75, 28.48 (2C).

EXAMPLE 5

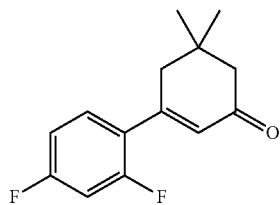

5 p-Toluenesulfonyl chloride (1.77 g, 9.27 mmol), dimedone (1.00 g, 7.13 mmol) and potassium carbonate (2.46 g, 17.8 mmol) in a 2:1 ratio of 1,4-dioxane (14 mL) and water (7 mL) were reacted as described in General Procedure A. To this mixture was added 2,4-difluorophenylboronic acid (1.35 g, 8.56 mmol) and tetrakis(triphenylphosphine) palladium (0) (247 mg, 0.21 mmol) and the mixture was heated under reflux for 3 hours. Usual workup and purification by silica gel chromatography afforded 0.73 g, (43%) of the compound of example 5 as a beige solid. $^1$H NMR (400 MHz, CDCl$_3$) δ, ppm: 7.31 (dt, J=8.62, 6.36 Hz, 1H), 6.96-6.82 (m, 2H), 6.24 (s, 1H), 2.60 (t, J=1.61 Hz, 2H), 2.34 (s, 2H), 1.12 (s, 6H). $^{13}$C NMR (100 MHz, CDCl$_3$) δ, ppm: 199.58, 163.40, 160.15, 153.86, 129.92, 127.89, 124.29, 111.81, 104.79, 51.00, 43.67, 34.15, 28.17 (2C).

EXAMPLE 6

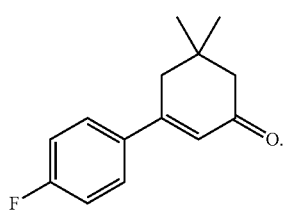

6

Following General Procedure, the use of p-toluenesulfonyl chloride (1.42 g, 7.42 mmol) dimedone (800 mg, 5.71 mmol), potassium carbonate (1.97 g, 14.3 mmol) in a 2:1 ratio of 1,4-dioxane (12 mL) and water (6 mL) followed by 4-fluorophenylboronic acid (1.08 g, 6.85 mmol) and tetrakis(triphenylphosphine)palladium(0) (197 mg, 0.17 mmol) following General Procedure A gave after purification 0.71 g (57%) of compound of example 6 as a light-brown solid.

$^1$H NMR (400 MHz, CDCl$_3$) δ, ppm: 7.56-7.43 (m, 2H), 7.13-6.97 (m, 2H), 6.33 (t, J=1.39 Hz, 1H), 2.59 (d, J=1.45 Hz, 2H), 2.30 (s, 2H), 1.10 (s, 6H). $^{13}$C NMR (100 MHz, CDCl$_3$) δ, ppm: 199.87, 164.98, 162.49, 156.25, 135.05, 128.04, 124.21, 115.89, 115.67, 50.80, 42.35, 33.71, 28.37 (2C).

HRMS. Calculated for C14HH$_{15}$FO: 218.1107. Found: 218.1091

EXAMPLE 7

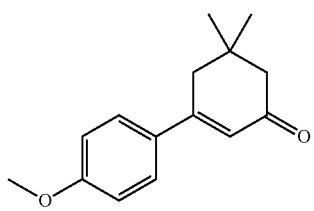

7 p-Toluenesulfonyl chloride (247.8 mg, 1.3 mmol) was added to a mixture of dimedone (140.2 mg, 1.0 mmol) and potassium carbonate (345 mg, 2.5 mmol) in a 2:1 ratio of 1,4-dioxane (4 mL) and water (2 mL). This mixture was stirred at room temperature for 1 hour. 4-Methoxyphenyl boronic acid (182.4 mg, 1.2 mmol) and tetrakis(triphenylphosphine)palladium(0) (34.7 mg, 0.03 mmol) were added and the mixture was heated under reflux for 2 hours. The resulting mixture was extracted with EtOAc (3×10 mL). The extract was dried with MgSO$_4$, filtered and the solvents were evaporated via rotary evaporator. The compound of example 7 was isolated via column chromatography to yield 130 mg (56%) of white crystals.

¹H NMR (400 MHz, CDCl₃) δ, ppm: 7.51-7.40 (m, 2H), 6.89-6.84 (m, 2H), 6.32 (s, 1H), 3.77 (s, 3H), 2.55 (d, J=1.25 Hz, 2H), 2.25 (s, 2H), 1.06 (s, 6H). ¹³C NMR (100 MHz, CDCl₃) δ, ppm: 199.94, 161.03, 156.92, 130.72, 127.48 (2C), 122.24, 113.93 (2C), 55.14, 50.59, 41.79, 33.38, 28.21 (2C).

HRMS. Calculated for C₁₅H₁₈O₂; 230.1307. Found: 230.1323

EXAMPLE 8

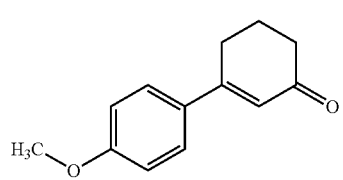

A mixture of p-TsCl (1.6 equiv, 440 mg, 2.31 mmol), 1-3-cylohexanedione (1.2 equiv, 200 mg, 1.78 mmol) and potassium carbonate (2.5 equiv, 511 mg, 3.7 mmol) was stirred in 1,4-dioxane (10 ml) and water (5 ml) until deemed complete by TLC. 4-Methoxyphenylboronic acid 225 mg and 8.55 mg of Pd(PPh₄)₄ was added and the reaction mixture was refluxed at 100° C. for 1.5 hours. The usual workup described in General Procedure A followed by flash column chromatography eluting with EtOAc/hexane (15-35%) afforded the compound of example 8 as white crystals 67% yield.

¹H NMR (400 MHz, CDCl₃) δ ppm: 7.51 (dt, J=9.9, 2.6 Hz, 2H), 6.92 (dt, J=9.9, 2.6 Hz, 2H), 6.39 (t, J=1.3 Hz, 1H), 3.84 (s, 3H), 2.75 (td, J=9.1, 1.3 Hz, 2H), 2.46 (t, J=6.7 Hz, 2H), 2.13 (m, J=6.4 Hz, 2H). ¹³C NMR (100 MHz, CDCl₃) δ ppm: 199.91, 161.24, 159.11, 130.84, 127.64, 123.74, 114.16, 55.40, 37.21, 27.88, 22.79

HRMS. Calculated for C₁₃H₁₄O₂: 202.0994. Found: 202.0997

EXAMPLE 9

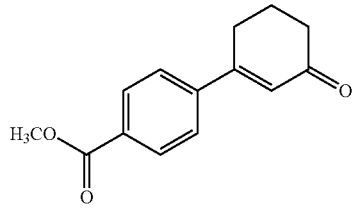

A mixture of p-TsCl (1.6 equiv, 371.8 mg, 1.95 mmol), 1-3-cylohexanedione (1.2 equiv, 168.2 mg, 1.5 mmol) and potassium carbonate (2.5 equiv, 431.9 mg, 3 mmol) in 1,4-dioxane (10 ml) and water (5 ml) was stirred at room temperature until deemed complete by TLC. 4-methoxycarbonylphenylboronic acid 225 mg and 7.22 mg of Pd(PPh₄)₄ was added and the reaction mixture was refluxed at 100° C. for 1.5 hours. Usual workup followed by flash chromatography of the crude product EtOAc/hexane (15-30%) gave 90 mg of the compound of example 9 as white crystals (31%).

¹H NMR (400 MHz, CDC₃) δ ppm: 8.06 (dt, J=8.6, 1.9 Hz, 2H), 7.58 (dt, J=8.6, 1.9 Hz, 2H), 6.44 (t, J=1.5 Hz, 1H), 3.93 (s, 3H), 2.78 (td, J=6.0, 1.5 Hz, 2H), 2.50 (t, J=6.7 Hz, 2H), 2.17 (m, J=5.4 Hz, 2H). ¹³C NMR (100 MHz, CDCl₃) δ ppm: 199.55, 166.44, 158.38, 143.20, 131.19, 129.95 (2C), 126.78 (2C), 126.04, 52.29, 37.23, 28.08, 22.73

HRMS. Calculated for C₁₄H₁₄O₃: 230.0943. Found: 230.0975

EXAMPLE 10

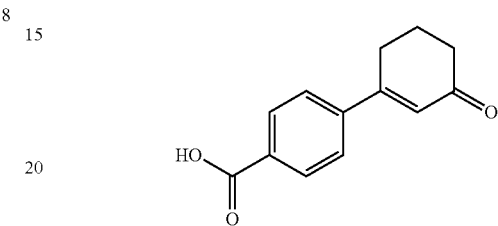

The ester compound of example 2 (1 equiv, 20 mg, 0.087 mmol) was added to a solution of 1 mL of 5% NaOH in 4 mL of methanol. The solution was kept at room temperature overnight. The reaction mixture was diluted with 20 ml of EtOAc. A 5% HCl solution was added to the separated aqueous layer until the solution became acidic. This mixture was extracted with 20 ml of EtOAc. The organic layer was dried using anhydrous MgSO₄ and concentrated under reduced pressure to afford the compound of example 10 as a copper coloured solid (10 mg, 0.046 mmol, 53%).

¹H NMR (400 MHz, CDCl₃) δ ppm: 8.07 (d, J=8.5 Hz, 2H), 7.72 (d, J=8.5 Hz, 2H), 6.44 (s, 1H), 2.87 (td, J=6.0, 1.2 Hz, 2H), 2.50 (t, J=6.7 Hz, 2H), 2.18 (m, J=6.3 Hz, 2H) ¹³C NMR (100 MHz, CDCl₃) δ ppm: 201.07, 167.72, 160.63, 143.12, 131.77, 129.74, 127.72, 126.00, 38.16, 36.63, 30.29, 27.69, 22.43

EXAMPLE 11

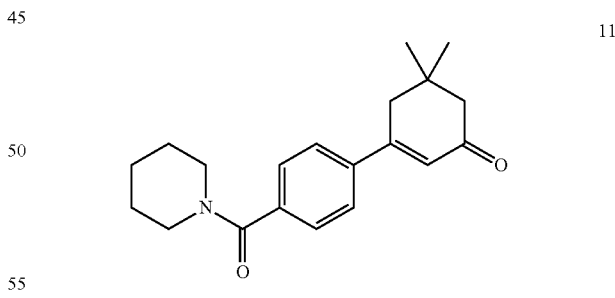

3',3'-Dimethyl-5'-oxo-2',3',4',5'-tetrahydro-[1,1'-biphenyl]-4-carboxylic acid (example 2) (0.1 g, 0.41 mmol) was added to dichloromethane (15 mL). Thionyl chloride (81.9 mg, 0.69 mmol) was added and the mixture was refluxed for 3 hours. The solvent and excess thionyl chloride were evaporated using a rotary evaporator. The flask was closed using a septum and the mixture was dissolved in benzene (15 mL) at 0° C. Piperidine (70.0 mg, 0.82 mmol) and triethylamine (82.8 mg, 0.82 mmol) were very slowly added simultaneously and the mixture was stirred for 5 minutes at 0° C. The reaction was quenched with water and an aqueous solution of NH₄Cl. The mixture was extracted with EtOAc (3×10 mL), dried with MgSO₄ and filtered. The extract was treated with an aqueous solution of 5% sodium hydroxide. The amide compound of example 11 was obtained in 70% yield as a white fine powder.

¹H NMR (400 MHz, CDCl₃) δ, ppm: 7.59-7.52 (m, 2H), 7.46-7.41 (m, 2H), 6.42 (t, J=1.45 Hz, 1H), 3.78-3.66 (br, 2H), 3.43-3.28 (br, 2H), 2.64 (d, J=1.42 Hz, 2H), 2.35 (s, 2H), 1.72-1.61 (m, 4H), 1.57-1.49 (m, 2H), 1.13 (s, 6H). ¹³C NMR (100 MHz, CDCl₃) δ, ppm: 199.90, 169.43, 156.61, 140.05, 137.88, 127.27 (2C), 126.24 (2C), 124.96, 50.92 (2C), 42.30 (2C), 33.77 (2C), 28.38 (2C), 24.54 (2C)

HRMS. Calculated for C₂₀H₂₅ NO₂: 311.1885. Found: 311.1863

EXAMPLE 12

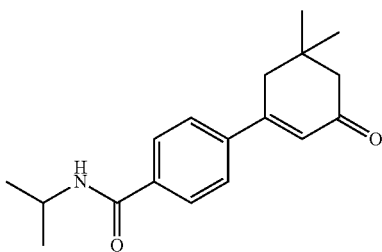

3',3'-dimethyl-5'-oxo-2',3',4',5'-tetrahydro-[1,1'-biphenyl]-4-carboxylic acid (example 2) (75 mg, 0.31 mmol) was added to dichloromethane (15 mL). Thionyl chloride (62.1 mg, 0.52 mmol) was added and the mixture was refluxed for 3 hours. The solvent and excess thionyl chloride were evaporated using a rotary evaporator. The flask was closed using a septum and the mixture was dissolved in benzene (15 mL) at 0° C. Isopropylamine (72.7 mg, 1.23 mmol) and triethylamine (124 mg, 1.23 mmol) were very slowly added simultaneously and the mixture was stirred for 5 minutes at 0° C. The reaction was quenched with water and an aqueous solution of NH₄Cl. The mixture was extracted with EtOAc (3×10 mL), dried with MgSO₄ and filtered and the ethyl acetate layer was washed 5% sodium hydroxide. The isopropyl amide compound of example 12 was isolated by column chromatography in 57% yield (50 mg) as a white fine powder.

¹H NMR (400 MHz, CDCl₃) δ, ppm: 7.79 (d, J=8.37 Hz, 2H), 7.57 (d, J=8.37 Hz, 2H), 6.42 (s, 1H), 5.95 (d, J=6.25 Hz, 1H), 4.30 (qd, J=13.30, 6.56 Hz, 1H), 2.65 (d, J=1.15 Hz, 2H), 2.35 (s, 2H), 1.28 (d, J=6.55 Hz, 6H), 1.14 (s, 6H). ¹³C NMR (100 MHz, CDCl₃) δ, ppm: 199.84, 165.78, 156.34, 141.81, 136.00, 127.28 (2C), 126.24 (2C), 125.30, 50.89, 42.23, 42.03, 33.77, 28.36 (2C), 22.80 (2C)

EXAMPLE 13

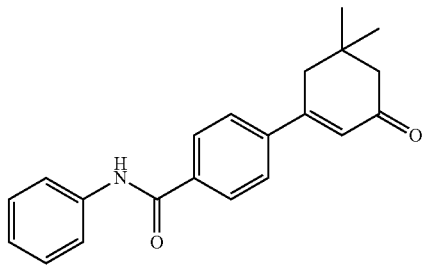

3',3'-dimethyl-5'-oxo-2',3',4',5'-tetrahydro-[1,1'-biphenyl]-4-carboxylic acid (example 2) (100 mg, 0.41 mmol) was added to dichloromethane (15 mL). Thionyl chloride (82.7 mg, 0.70 mmol) was added and the mixture was refluxed for 3 hours. The solvent and excess thionyl chloride were evaporated using a rotary evaporator. The flask was closed using a septum and the mixture was dissolved in benzene (15 mL) at 0° C. Aniline (152 mg, 1.64 mmol) and triethyl amine (166 mg, 1.64 mmol) were very slowly added simultaneously and the mixture was stirred for 5 minutes at 0° C. The reaction was quenched with water and an aqueous solution of NH₄Cl. The mixture was extracted with EtOAc (3×10 mL), dried with MgSO₄ and filtered. The extract was treated with an aqueous solution of 5% sodium hydroxide. The anilide compound of example 13 was isolated by column chromatography as a white fine powder (50 mg) in 38% yield.

¹H NMR (400 MHz, CDCl₃) δ, ppm: 7.95-7.90 (m, 2H), 7.83 (br, 1H), 7.68-7.61 (m, 4H), 7.42-7.36 (m, 2H), 7.21-7.15 (m, 1H), 6.45 (t, J=1.44 Hz, 1H), 2.67 (d, J=1.45 Hz, 2H), 2.37 (s, 2H), 1.16 (s, 3H). ¹³C NMR (100 MHz, CDCl₃) δ, ppm: 199.85, 164.81, 156.14, 142.47, 137.75, 135.99, 129.18 (2C), 127.52 (2C), 126.56 (2C), 125.61, 124.81, 120.24 (2C), 50.94, 42.29, 33.84, 28.41 (2C)

EXAMPLE 14

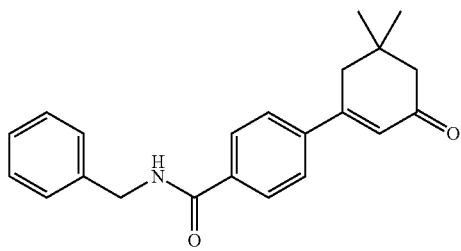

3',3'-dimethyl-5'-oxo-2',3',4',5'-tetrahydro-[1,1'-biphenyl]-4-carboxylic acid (example 2) (100 mg, 0.41 mmol) was added to dichloromethane (15 mL). Thionyl chloride (82.7 mg, 0.70 mmol) was added and the mixture was refluxed for 3 hours. The solvent and excess thionyl chloride were evaporated using a rotary evaporator. The flask was closed using a septum and the mixture was dissolved in benzene (15 mL) at 0° C. Benzyl amine (175 mg, 1.64 mmol) and triethyl amine (166 mg, 1.64 mmol) were very slowly added simultaneously and the mixture was stirred for 5 minutes at 0° C. The reaction was quenched with water and an aqueous solution of NH₄Cl. The mixture was extracted with EtOAc (3×10 mL), dried with MgSO₄ and filtered. The extract was treated with an aqueous solution of 5% sodium hydroxide. The compound of example 14 was isolated by column chromatography to obtain as a beige fine powder (70 mg, 51%).

¹H NMR (400 MHz, CDCl₃) δ, ppm: 7.85-7.81 (m, 2H), 7.60-7.55 (m, 2H), 7.38-7.28 (m, 5H), 6.49-6.43 (m, 1H), 6.42 (t, J=1.44 Hz, 1H), 4.66 (d, J=5.64 Hz, 2H), 2.64 (d, J=1.43 Hz, 2H), 2.35 (s, 2H), 1.14 (s, 6H). ¹³C NMR (100 MHz, CDCl₃) δ, ppm: 199.82, 166.43, 156.21, 142.18, 137.94, 135.35, 128.86 (2C), 127.97 (2C), 127.76, 127.40 (2C), 126.37 (2C), 125.46, 50.91, 44.26, 42.26, 33.80, 28.38 (2C)

EXAMPLE 15

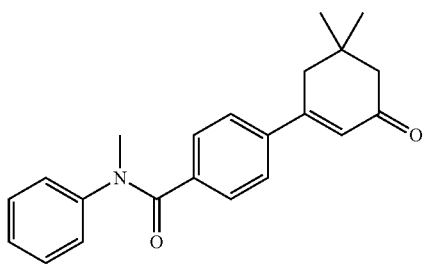

3',3'-Dimethyl-5'-oxo-2',3',4',5'-tetrahydro-[1,1'-biphenyl]-4-carboxylic acid (example 2) (100 mg, 0.41 mmol) was added to dichloromethane (15 mL). Thionyl chloride (82.7 mg, 0.70 mmol) was added and the mixture was refluxed for 3 hours. The solvent and excess thionyl chloride were evaporated using a rotary evaporator. The flask was closed using a septum and the mixture was dissolved in benzene (15 mL) at 0° C. N-methylaniline (175 mg, 1.64 mmol) and triethyl amine (166 mg, 1.64 mmol) were very slowly added simultaneously and the mixture was stirred for 5 minutes at 0° C. The reaction was quenched with water and an aqueous solution of NH₄Cl. The mixture was extracted with EtOAc (3×10 mL), dried with MgSO₄ and filtered. The extract was treated with an aqueous solution of 5% sodium hydroxide. The tertiary amide compound of example 15 was isolated by column chromatography to obtain a beige fine powder (60 mg, 44%).

¹H NMR (400 MHz, CDCl₃) δ, ppm: 7.33 (s, 4H), 7.28-7.22 (m, 2H), 7.19-7.14 (m, 1H), 7.07-7.03 (m, 2H), 6.32 (t, J=1.48 Hz, 1H), 3.51 (s, 3H), 2.55 (d, J=1.47 Hz, 2H), 2.30 (s, 2H), 1.09 (s, 6H). ¹³C NMR (100 MHz, CDCl₃) δ, ppm: 199.83, 169.67, 156.34, 144.64, 140.02, 137.23, 129.32 (2C), 129.17 (2C), 126.89 (2C), 126.76, 125.49 (2C), 124.99, 50.88, 42.07, 38.46, 33.66, 28.36 (2C)

EXAMPLE 16

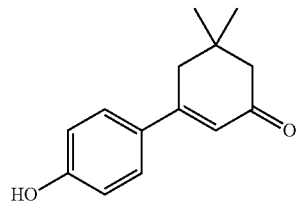

4-Bromophenol (4.33 g, 25 mmol) and imidazole (2.21 g, 32.5 mmol) were dissolved in a 1:1 ratio mixture of tetrahydrofuran (15 mL) and dimethylformamide (15 mL). tert-Butyldimethylsilyl chloride (4.15 g, 27.5 mmol) and 4-dimethylaminopyridine (trace amount) were added and the reaction was stirred for 12 hours at room temperature. The mixture was diluted with water (30 mL) and ether (40 mL) and then extracted with EtOAc (3×20 mL). The organic extracts were dried with MgSO₄, filtered and evaporated using a rotary evaporator. The silyl protected intermediate was isolated by column chromatography (5.63 g, 68%). The silyl protected intermediate (320 mg, 0.97 mmol) was dissolved in EtOAc (25 mL) and an aqueous 5% sodium hydroxide solution (25 mL) was added. The aqueous phase was kept and treated with an aqueous 10% hydrochloric acid solution (15 mL). This mixture was extracted with EtOAc (3×10 mL) and this organic extract was dried with MgSO₄, filtered and evaporated to obtain the compound of example 16 as a beige solid. (150 mg, 71%)

Total synthesis yield=48%

¹H NMR (300 MHz, MeOH-D₄) δ, ppm: 7.57-7.48 (m, 2H), 6.94-6.73 (m, 2H), 6.34 (t, J=1.39 Hz, 1H), 2.70 (d, J=1.36 Hz, 2H), 2.32 (s, 2H), 1.12 (s, 6H). ¹³C NMR (100 MHz, MeOH-D₄) δ, ppm: 201.62, 159.83, 159.79, 129.37, 127.78 (2C), 120.58, 115.26 (2C), 50.18, 41.44, 33.13, 27.10 (2C)

HRMS. Calculated for C14H 16O2: 216.1150. Found: 216.1174

EXAMPLE 17

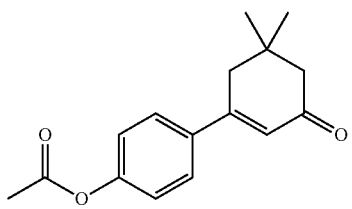

4'-Hydroxy-5,5-dimethyl-5,6-dihydro-[1,1'-biphenyl]-3 (4H)-one (50 mg, 0.23 mmol) was dissolved in dichloromethane (10 mL) and 4-dimethylaminopyridine (trace amounts) was added. Acetic anhydride (27.7 mg, 0.46 mmol) and triethylamine (70.1 mg, 0.69 mmol) were added and the solution was stirred for 30 minutes at room temperature. The reaction mixture was then poured into a flask containing a saturated aqueous solution of NaHCO₃ and extracted with dichloromethane (3×10 mL). The organic extract was dried with MgSO₄, filtered and evaporated. The acetate compound of example 17 was isolated by column chromatography as a light-beige solid in 42% yield.

$^1$H NMR (400 MHz, CDCl$_3$) δ, ppm: 7.59-7.50 (m, 2H), 7.20-7.06 (m, 2H), 6.38 (s, 1H), 2.62 (d, J=1.25 Hz, 2H), 2.33 (s, 2H), 2.31 (s, 3H), 1.12 (s, 6H). $^{13}$C NMR (100 MHz, CDCl$_3$) δ, ppm: 199.93, 169.20, 156.45, 151.89, 136.62, 127.36 (2C), 124.43, 121.95 (2C), 50.87, 42.32, 33.76, 28.38 (2C), 21.10

General Scheme B

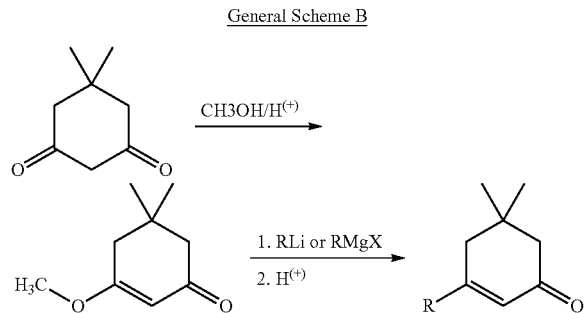

EXAMPLE 18

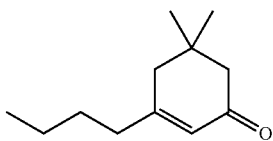

3-Methoxy-5,5-dimethylcyclohex-2-enone (1.0 g, 6.48 mmol) was dissolved in dry THF at 0° C. under nitrogen atmosphere. n-Butyllithium 2.5M (6.7 mL, 114.93 mmol) was slowly added and the solution was stirred for 20 minutes at 0° C. The mixture was quenched with aqueous NH$_4$Cl solution and extracted with EtOAc (3×10 mL). The resulting extract was dried with MgSO$_4$, filtered and evaporated. The compound of example 18, 3-Butyl-5,5-dimethylcyclohex-2-en-1-one, was isolated in 32% yield as a colorless oil by column chromatography (370 mg).

$^1$H NMR (400 MHz, CDCl$_3$) δ, ppm: 5.87 (s, 1H), 2.18 (m, 6H), 1.47 (m, 2H), 1.33 (qd, J=14.36, 7.15 Hz, 2H), 1.02 (s, 6H), 0.91 (t, J=7.28 Hz, 3H).

$^{13}$C NMR (50 MHz, CDCl$_3$) δ, ppm: 200.0, 164.2, 124.4, 51.0, 43.8, 37.6, 33.5, 28.9, 28.2, 22.2, 13.7

EXAMPLE 19

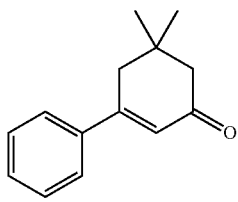

Magnesium turnings (0.30 g, 12.3 mmol) are added to a flask and put under nitrogen atmosphere. A solution of bromobenzene (1.50 g, 9.55 mmol) in dry diethyl ether (10 mL) is added and the mixture is lightly refluxed until all the magnesium turnings are consumed. A solution of 3-methoxy-5,5-dimethylcyclohex-2-enone (0.50 g, 3.24 mmol) in diethyl ether (10 mL) is added at room temperature and the mixture is refluxed again for 30 minutes. The reaction is quenched using water and a saturated aqueous solution of NH$_4$Cl. The mixture is extracted with EtOAc, dried with MgSO$_4$, filtered and evaporated to afford the compound of example 19, 3-phenyl-5,5-dimethylcyclohex-2-en-1-one, as a white solid (260 mg, 40%) after silica gel chromatography.

$^1$H NMR (400 MHz, CDCl$_3$) δ, ppm: 7.54 (ddd, J=4.48, 2.39, 1.40 Hz, 2H), 7.43-7.40 (m, 3H), 6.42 (t, J=1.50, 1.50 Hz, 1H), 2.66 (d, J=1.46 Hz, 2H), 2.35 (s, 2H), 1.14 (s, 6H); $^{13}$C NMR (100 M Hz, CDCl$_3$) δ, ppm: 199.7, 157.4, 138.9, 129.8, 128.6, 126.0, 124.3, 51.0, 42.4, 33.9, 28.5

HRMS. Calculated for C14H16O: 200.1201. Found=200.1187

EXAMPLE 20

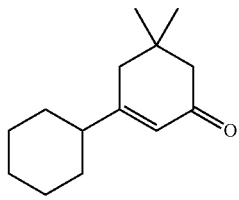

Magnesium turnings (0.43 g, 17.9 mmol) are added to a flask and put under nitrogen atmosphere. A solution of bromocyclohexane (2.91 g, 17.9 mmol) in dry diethyl ether (10 mL) is added and the mixture is lightly refluxed until all the magnesium turnings are consumed. A solution of 3-ethoxy-5,5-dimethylcyclohex-2-enone (1.0 g, 5.95 mmol) in diethyl ether (10 mL) is added at room temperature and the mixture is refluxed again for 30 minutes. The reaction is quenched using water and an aqueous solution of NH$_4$Cl. The mixture is extracted with EtOAc, dried with MgSO$_4$, filtered and evaporated to afford, after silica gel chromatography, the compound of example 20, 3-cyclohexyl-5,5-dimethylcyclohex-2-en-1-one, as a white solid (290 mg, 24%).

$^1$H NMR (400 MHz, CDCl$_3$) δ, ppm: 5.84 (d, J=0.69 Hz, 1H), 2.19 (s, 2H), 2.17 (d, J=0.86 Hz, 2H), 2.05-1.94 (m, 1H), 1.84-1.65 (m, 5H), 1.35-1.11 (m, 5H), 1.00 (s, 6H). $^{13}$C NMR (100 MHz, CDCl$_3$) δ, ppm: 200.56, 168.67, 122.92, 51.26, 46.05, 42.58, 33.58, 30.78 (2C), 28.18 (2C), 26.21 (2C), 26.02

EXAMPLE 21

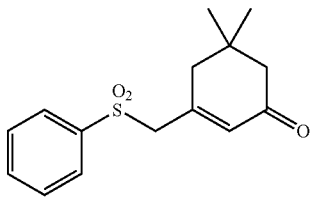 [SMILES: CC1(C)CC(=O)C=C(CS(=O)(=O)c2ccccc2)C1]

A mixture of 5-5-dimethyl-1,3-cyclohexanedione (1 equiv, 4 g, 28.5 mmol), p-TsCl (1 equiv, 5.44 g, 28.5 mmol) and potassium carbonate (2.5 equiv, 9.85 g, 71.25 mmol) in 60 ml of acetone was stirred at room temperature for 18 h. The mixture was filtered and concentrated under reduced pressure. The crude mass was purified by flash column chromatography eluting with EtOAc/hexane (20-25%) to afford 5.85 g of the intermediate sulfonate ester (70)% of a light brown oil.

¹H NMR (400 MHz, CDCl₃) δ ppm: 7.79 (dt, J=8.6, 1.9 Hz, 2H), 7.35 (dq, J=8.6, 1.5 Hz, 2H), 5.75 (t, J=1.3, 1H), 2.44 (s, 3H), 2.35 (d, J=1.3 Hz, 2H), 2.17 (s, 2H), 1.00 (s, 6H)

Methyl phenyl sulfone (2 equiv, 212 mg, 1.36 mmol) dissolved in 1 mL of dry THF was added to a solution of LDA (2 equiv, 0.68 ml, 1.36 mmol) dissolved in 15 ml of dry THF kept at −78° C. under nitrogen. The mixture was left to stir for 15 minutes. Compound 8 (1 equiv, 200 mg, 0.68 mmol) was dissolved in dry THF and added drop-wise and the solution was kept at the low temperature for 1 h. The reaction mixture was allowed to warm to room temperature, diluted with 20 mL of saturated NH4CL solution and extracted with 2×20 mL of EtOAc. The organic extracts were combined and washed with water (2×5 ml), dried with anhydrous MgSO₄ and concentrated under reduced pressure. The crude mass was purified by flash column chromatography eluting with EtOAc/hexane (40%) 0.1 g, 53% of the compound of example 21 as a to yellow oil.

¹H NMR (400 MHz, CDCl₃) δ ppm: 7.82 (d, J=7.2 Hz, 2H), 7.63 (m, 1H), 7.52 (t, J=7.7 Hz, 2H), 5.55 (s, 1H), 3.89 (s, 2H), 2.38 (d, J=1.0 Hz, 2H), 2.14 (s, 2H), 0.98 (s, 6H) ¹³C NMR (100 MHz, CDCl₃) δ ppm: 198.68, 148.35, 138.01, 134.33, 131.52, 129.37, 128.23, 63.88, 50.71, 43.85, 33.63, 28.08

EXAMPLE 22

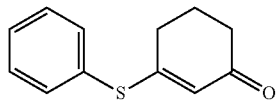 [SMILES: O=C1C=C(Sc2ccccc2)CCC1]

Thiophenol (3.77 g, 34.2 mmol), 5,5-dimethylcyclohexane-1,3-dione (4.0 g, 28.5 mmol) and anhydrous ferrous chloride (0.93 g, 5.71 mmol) were added to a flask and stirred at room temperature for 5 hours. The mixture was dissolved in dichloromethane (30 mL) and washed with a 10% sodium hydroxide solution in an extraction funnel. The aqueous phase was treated with bleach to get rid of the strong thiophenol smell. The organic phase was dried with MgSO₄, filtered and concentrated via rotary evaporator. The compound of example 22, 3-(phenylthio)cyclohex-2-enone, was isolated via column chromatography (1.78 g, 30%).

¹H NMR (400 MHz, CDCl₃) δ, ppm: 7.48-7.34 (m, 5H), 5.45 (t, J=1.14 Hz, 1H), 2.50 (dd, J=8.76, 3.48 Hz, 2H), 2.35 (dd, J=8.23, 4.93 Hz, 2H), 2.01 (m, 2H)

EXAMPLE 23

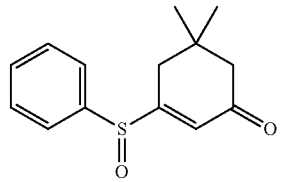 [SMILES: CC1(C)CC(=O)C=C(S(=O)c2ccccc2)C1]

5,5-dimethyl-3-(phenylthio)cyclohex-2-enone (1.09 g, 4.69 mmol) was dissolved in dichloromethane (15 mL) and the solution was cooled to 0° C. mCPBA was dissolved in a small amount of dichloromethane and added dropwise. The mixture was stirred over 30 mins at 0° C., then warmed to room temperature and stirred for an additional 1 hour. The reaction was quenched with a 10% aqueous solution of sodium carbonate. The mixture was extracted with dichloromethane (2×10 mL) and washed a last time with a solution of brine (20 mL). The organic extract was dried with MgSO₄, filtered and concentrated via rotary evaporator. The sulfoxide compound of example 23 was isolated using column chromatography to obtain a clear yellow oil (550 mg, 47%)

¹H NMR (400 MHz, CDCl₃) δ, ppm: 7.66-7.60 (m, 2H), 7.55-7.49 (m, 3H), 6.74 (t, J=1.59 Hz, 1H), 2.26 (d, J=1.27 Hz, 2H), 2.06 (dq, J=17.76, 1.54 Hz, 2H), 0.91 (s, 3H), 0.85 (s, 3H)

EXAMPLE 24

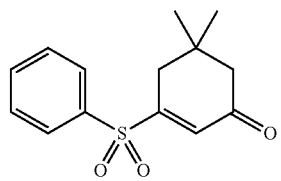 [SMILES: CC1(C)CC(=O)C=C(S(=O)(=O)c2ccccc2)C1]

5,5-dimethyl-3-(phenylthio)cyclohex-2-enone (1.09 g, 4.69 mmol) was dissolved in dichloromethane (15 mL) and the solution was cooled to 0° C. mCPBA was dissolved in a small amount of dichloromethane and added dropwise. The mixture was stirred over 30 mins at 0° C., then warmed to room temperature and stirred for an additional 1 hour. The reaction was quenched with a 10% aqueous solution of sodium carbonate. The mixture was extracted with dichloromethane (2×10 mL) and washed a last time with a solution of brine (20 mL). The organic extract was dried with MgSO₄, filtered and concentrated via rotary evaporator. The sulfone compound of example 24 was isolated using column chromatography to obtain a clear yellow oil (300 mg, 24%)

¹H NMR (400 MHz, CDCl₃) δ, ppm: 7.90 (ddd, J=7.22, 2.93, 1.67 Hz, 2H), 7.70 (m, 1H), 7.62-7.57 (m, 2H), 6.72 (t, J=1.73 Hz, 1H), 2.39 (d, J=1.75 Hz, 2H), 2.27 (s, 2H), 0.96 (s, 6H)

EXAMPLE 25

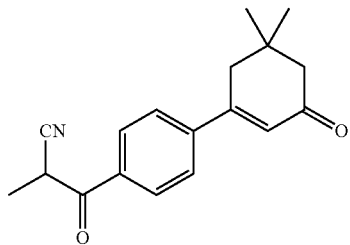 [SMILES: CC(C#N)C(=O)c1ccc(C2=CC(=O)CC(C)(C)C2)cc1]

Lithium Diisopropylamide 2M (3.87 mL, 7.74 mmol) was added to dry THF (25 mL) under nitrogen atmosphere at −78° C. Propionitrile (0.06 mL, 7.74 mmol) was added dropwise and the solution was stirred at −78° C. for 15 minutes. 3',3'-dimethyl-5'-oxo-2',3',4',5'-tetrahydro-[1,1'-biphenyl]-4-carboxylic acid (100 mg, 0.387 mmol) was added dropwise and the solution was stirred for 30 minutes. The mixture was quenched by transferring it to a beaker containing an aqueous $NH_4Cl$ solution. The mixture was then warmed at room temperature and diluted with water followed by extraction with EtOAc (3×10 mL). The extract was dried with $MgSO_4^-$, filtered and concentrated by rotary evaporator.

The hydroxyl intermediate was isolated by column chromatography, dissolved in toluene, and p-toluenesulfonic acid (50 mg, catalytic) was added. The mixture was refluxed for 3 hours and was quenched by adding an aqueous $NaHCO_3$ solution. The mixture was extracted with EtOAc (3×10 mL) and the extract was dried with $MgSO_4$, filtered and evaporated by rotary evaporator. The compound of Example 25 was isolated by column chromatography (30 mg, 28%).

$^1$H NMR (400 MHz, $CDCl_3$) δ, ppm: 8.07-7.98 (m, 2H), 7.71-7.61 (m, 2H), 6.45 (s, 1H), 4.36 (q, J=7.18 Hz, 1H), 2.65 (d, J=1.53 Hz, 2H), 2.36 (d, J=5.96 Hz, 2H), 1.65 (d, J=7.14 Hz, 3H), 1.14 (s, 6H)

EXAMPLE 26

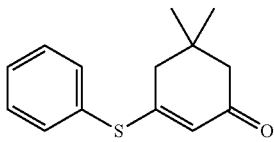 [SMILES: CC1(C)CC(=O)C=C(Sc2ccccc2)C1]

Thiophenol (3.77 g, 34.2 mmol), 5,5-dimethylcyclohexane-1,3-dione (4.0 g, 28.5 mmol) and anhydrous ferrous chloride (0.93 g, 5.71 mmol) were added to a flask and stirred at room temperature for 5 hours. The mixture was dissolved in dichloromethane (30 mL) and washed with a 10% sodium hydroxide solution in an extraction funnel. The aqueous phase was treated with bleach to get rid of the strong thiophenol smell. The organic phase was dried with $MgSO_4$, filtered and concentrated via rotary evaporator. The compound of Example 26, namely 5,5-dimethyl-3-(phenylthio)cyclohex-2-enone, was isolated via column chromatography (1.47 g, 22%).

$^1$H NMR (400 MHz, $CDCl_3$) δ, ppm: 7.45 (tdt, J=3.93, 2.51, 1.89 Hz, 5H), 5.48 (s, 1H), 2.40 (s, 2H), 2.23 (s, 2H), 1.08 (s, 6H)

The compounds described in the above examples display activity in in vitro and in vivo assays that track brain electrical activity. A first assay is conducted using voltage sensitive dye imaging. This is done on isolated rat brain slices kept viable in artificial cerebral spinal fluid (ACSF). Electrically stimulating the slice activates the neural assemblies therein. A voltage sensitive dye, such as, di-4-ANEPPS, is incubated with a brain slice for 1 hour in a suitable solution that enhances the dye penetration into the tissue. The dye reacts to changes in voltage across the cell membrane of the neurons in the brain slice. The example compounds are added to the ACSF at known concentration between 50 and 200 nM. The brain slices are then subjected to an electrical stimulus that activates the neurons in the slice. As the dye reacts to the change in voltage, which can be observed and quantified, the degree to which activation of the brain is dampened by the presence of the example compound is evaluated.

The compound of Example 1, exemplified above, was able to suppress activation of the brain slice activity by 29±5 and 48±5% at concentration of 50 and 200 nM respectively. The compound of Example 1 reduced both amplitude and duration of the response. This is indicative of the compounds ability to suppress brain activity.

FIG. 1 shows a summary of the activity of certain example compounds assayed in this manner. Many but not all compounds show higher activity at high brain activity than at lower frequencies. This is desirable attribute as excessive activity is a hallmark of seizure activity. The compound of example 1 is a particularly preferred example; having little or no activity at a stimulation frequency of 20 pulses/second while reducing activity by 48% at 60 pulses/second.

Figure 2:
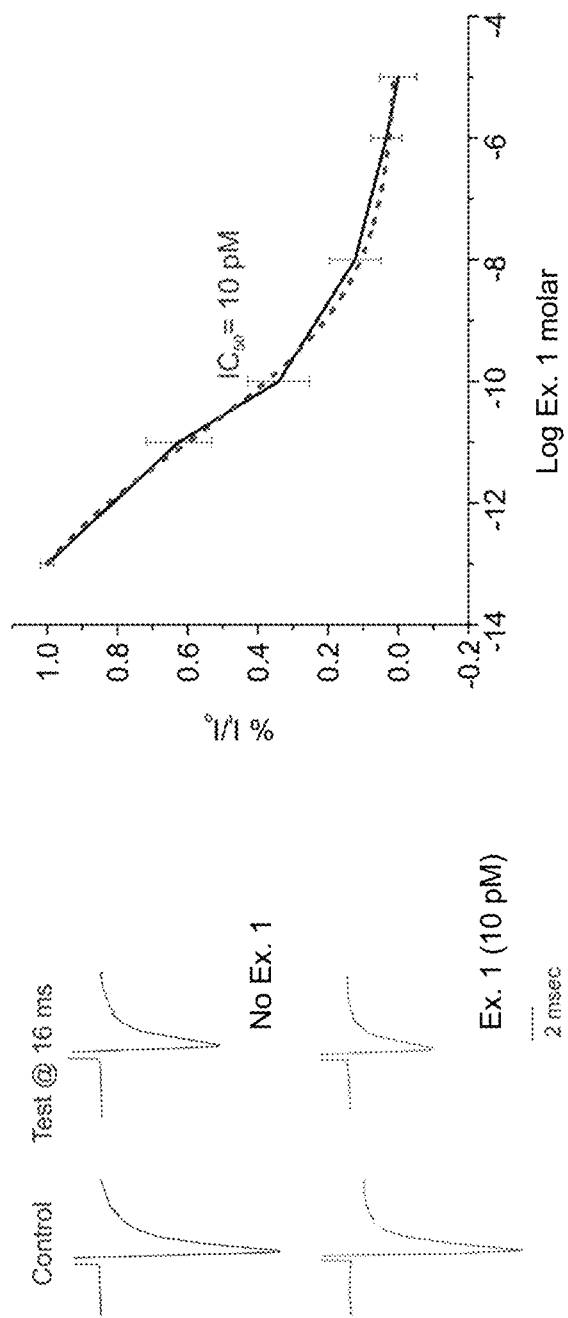
FIG. 2 is a graph showing the potency of the compound of Example 1 between 10 pM and 10 μM.

In another assay, the inhibition by the example compounds on the activity of voltage-gated sodium channels is determined using patch clamp electrophysiology. This analysis is done on cultured cortical neurons isolated from rats. As shown in FIG. 2, the potency of the compound of Example 1 was tested between 10 pM and 10 μM. This was done by assessing the suppression of the voltage gated sodium channel activity 16 ms after a test pulse.

The example compounds prolong the time required for voltage-gated sodium channels to recover from a normally occurring inactive state induced by depolarization. At high levels (frequency) of sodium channel activity these compounds are more effective in dampening activity than at low (non-seizure) levels of activity. Thus, the example compounds tend to suppress abnormal brain behavior to a higher degree than normal brain behavior.

Figure 3:
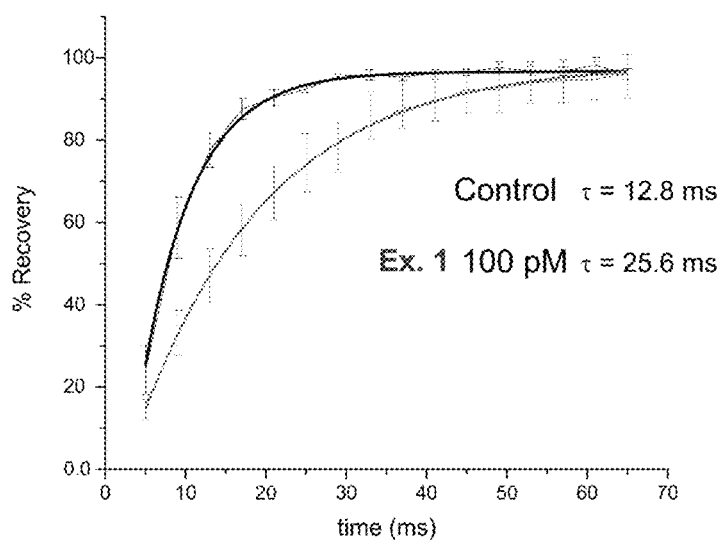
FIG. 3 is a graph showing the rate of recovery of the sodium channel activity before and after the application of 100 pM of the compound of Example 1.

As shown in FIG. 3, the compound of Example 1 slows the recovery of sodium channel inactivation. These data were obtained using the patch clamp technique on cultured rat cortical neurons. Under control conditions, recovery occurs at a rate of about 13 ms. In the presence of 100 pM of the compound of Example 1, recovery is slowed to a rate of about 26 ms, and recovery is substantially complete after about 50 ms. Additionally, FIG. 3 shows that recovery from inactivation is 100%. Accordingly, the compound of Example 1 does not cause partial inactivation of sodium channels at rest. This is a desirable property for antiseizure compounds, as little or no block of normal function occurs, while reducing (epileptic) activity that occurs at high frequency.

Figure 4:
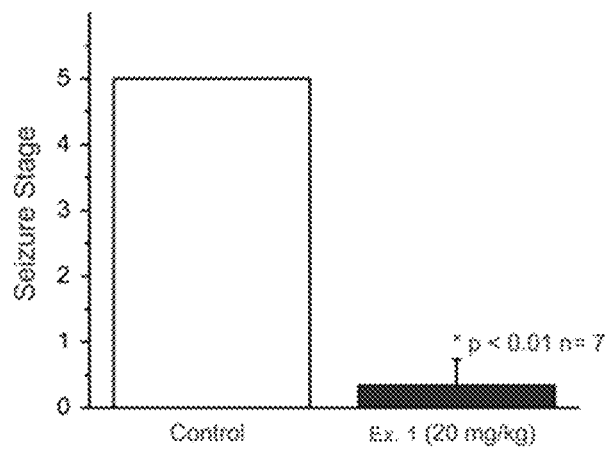
FIG. 4 is a summary of data showing the prevention, by the compound of Example 1 at a dose of 20 mg/kg, of stage 5 seizures in an animal model of partial complex seizures, using the amygdala kindling model of epilepsy.

As shown in FIG. 4, the compound of Example 1 attenuates seizures in a rodent kindling model of epilepsy. This model produces partial complex seizures that are similar to temporal lobe seizures experienced by humans. Oral administration (20 mg/kg) in the rodent model of amygdala stimulated kindling prevents stage 5 seizures from occurring.

Figure 5:
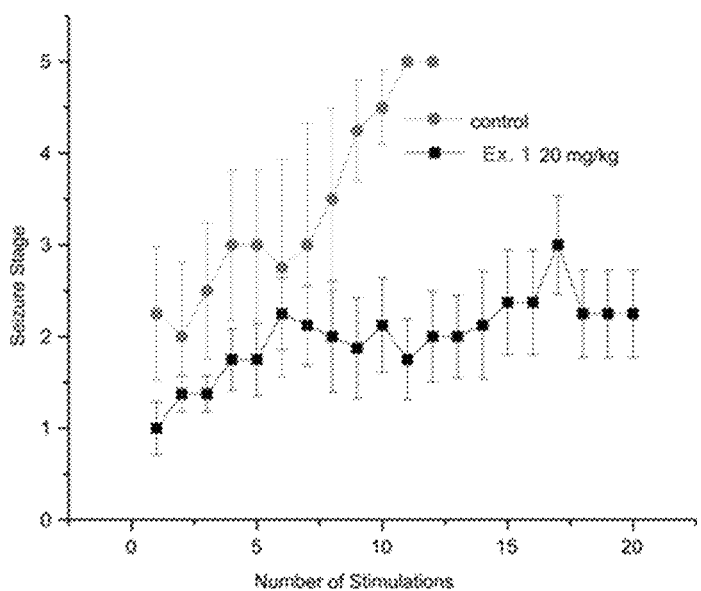
FIG. 5 is a graph showing that the pre-treatment of rats (20 mg/kg) undergoing the amygdala kindling procedure prevents the development of stage 5 seizures.

Further, as shown in FIG. 5, the compound of Example 1 is shown to impede the development of epileptic seizures in the kindling model. Prior prophylactic dosing of the compound of Example 1 prevents the onset of seizures in the kindling model. Therefore, compounds according to the present invention, including preferably the compound of Example 1, may be used in prophylactic treatment or prevention of epileptogenesis.

Figure 6:
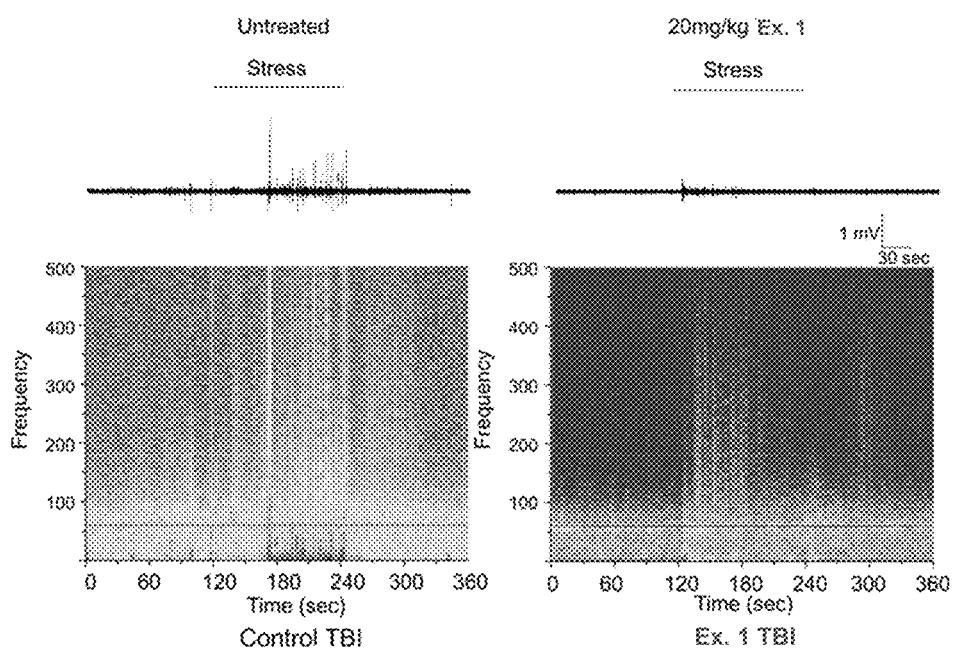
FIG. 6 is an electrographic record of activity from the amygdala of a rat which has undergone traumatic brain injury and has been stressed (tail pinch). The lower graph shows the frequencies and amplitude of the electrophysiological responses.

As shown in FIG. 6, the compound of Example 1 prevents the induction of seizure activity in a rodent model of traumatic brain injury/stress. After moderate traumatic brain injury under control conditions, stress induces epileptiform activity in the amygdala. This activity is shown on the left in FIG. 6, where a stressor induces increased activity. A fast Fourier transform sliding window spectrograph shown below the electrical response indicates that this activity extends into a range of frequencies up to 500 Hz (light grey/white indicates high amplitude power, while dark grey/black indicates low amplitude power). On the right in FIG. 6, it is evident that the compound of Example 1 prevents the induction of this response and is particularly effective in reducing high frequency activity (i.e. >250 Hz) that is considered to be epileptogenic. This electrophysiological response in the control traumatic brain injury rats was accompanied by stage 2 to 3 seizures (Racine scale: av. 2.0±0.5 n=6 rats). These behavioral responses were blocked in the traumatic brain injury rats treated with the compound of Example 1.

Figure 7:
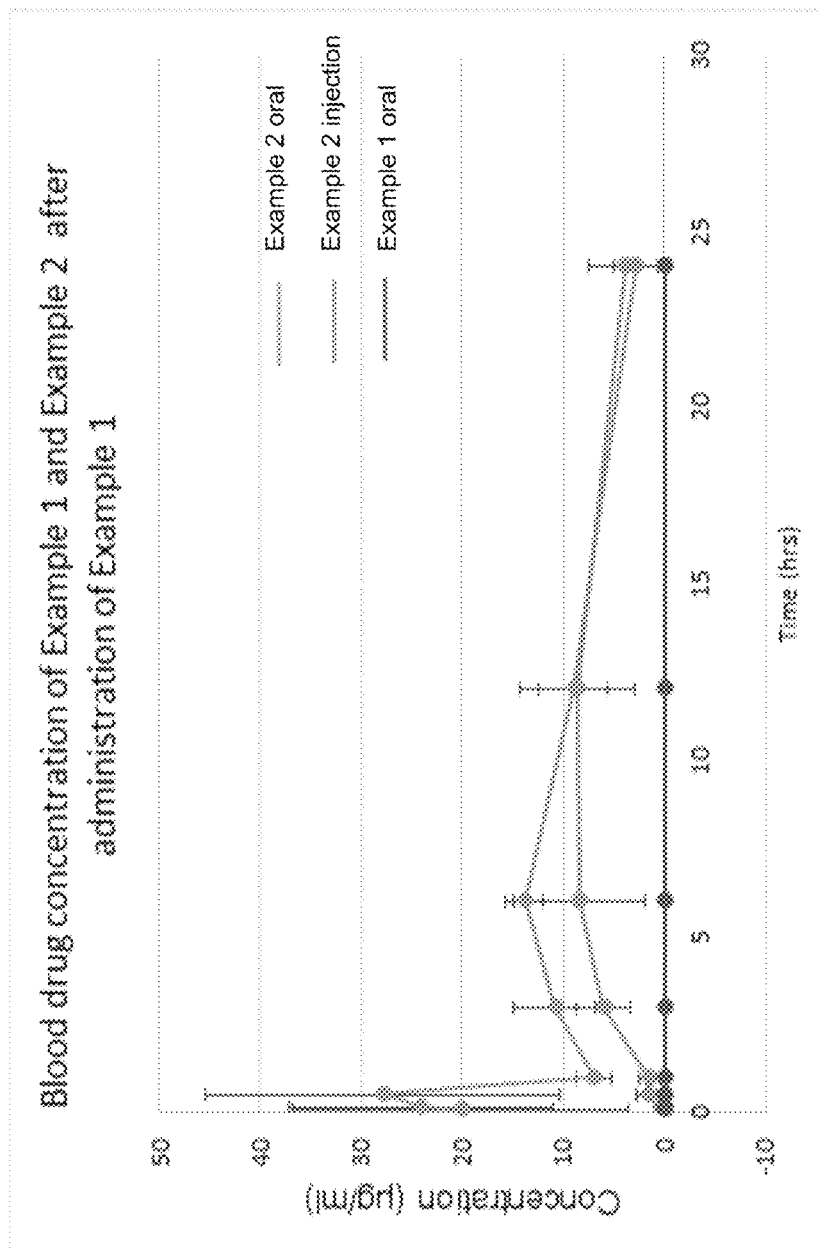
FIG. 7 is a graph showing the detection of the compounds of Example 1 and Example 2 in rat blood after oral or intravenous administration of the compound of Example 1.
Figure 8:
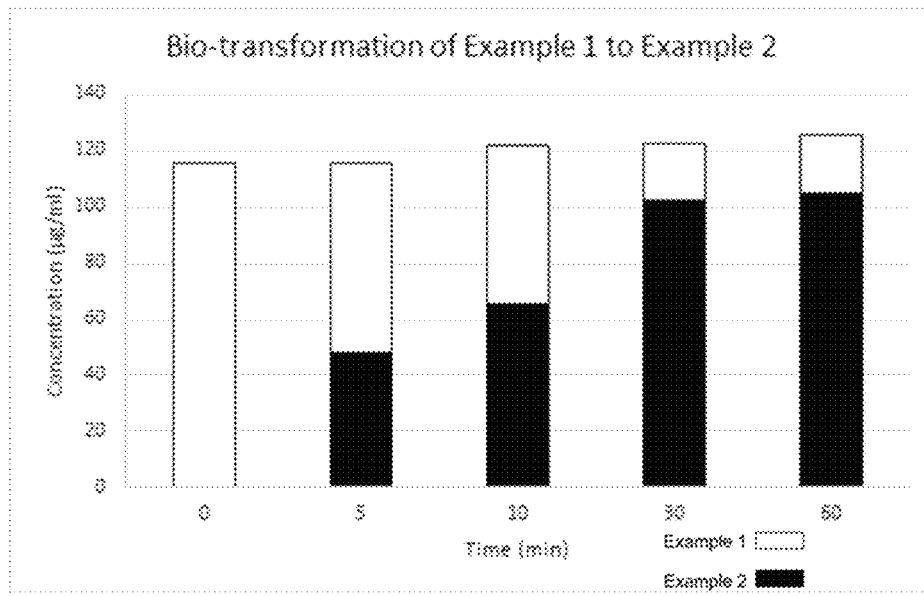
FIG. 8 is a graph showing the time it takes for the compound of Example 1 to be converted in vivo to the compound of Example 2.
Figure 9:
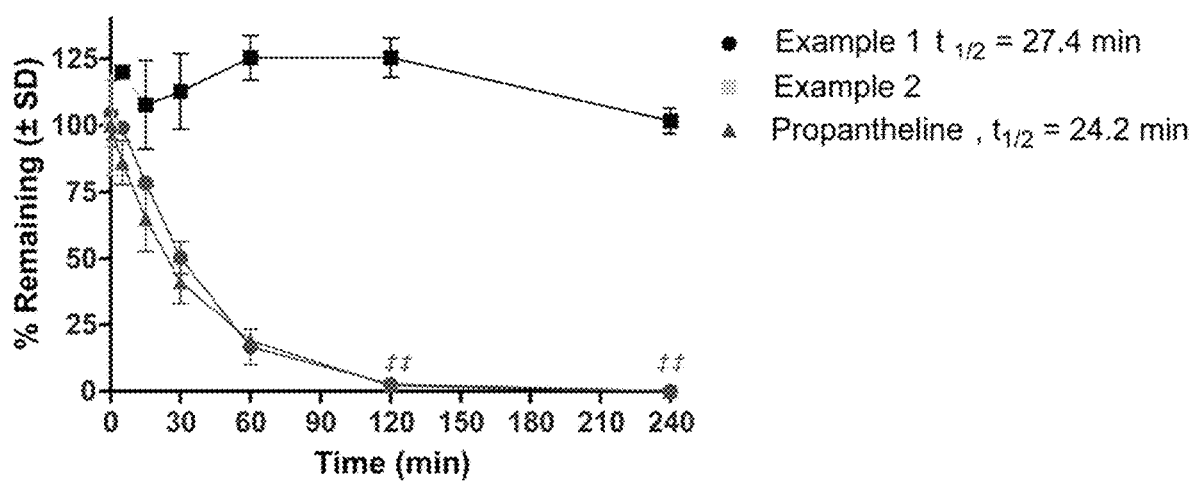
FIG. 9 is a graph showing the stability of the compound of Example 2 in human plasma once converted from the compound of Example 1.

As shown in FIGS. 7-9, there is data indicating that a prodrug/drug relationship exists between the compounds of Example 1 and Example 2. As shown in FIG. 7, injection or oral absorption of the compound of Example 1 is only detectable as the free acid (the compound of Example 2). All rats were dosed with the compound of Example 1 either orally or by vein injection. The compound of Example 2 was the only molecule detected in significant quantities over a period of 24 hours. These data indicate there is a prodrug-drug relationship between the compounds of Example 1 and Example 2. In vitro screening of the compound of Example 2 shows similar potency to the compound of Example 1, indicating that in vivo effects of the compound of Example 1 are likely mediated by the compound of Example 2.

As shown in FIG. 8, the time course of conversion of the compound of Example 1 to the compound of Example 2 is substantially complete within one hour of administration in rats dosed with 20 mg/kg of the compound of Example 1.

As shown in FIG. 9, the compound of Example 2 is stable and is not further converted to another molecule in human plasma dosed with the compound of Example 1.

Accordingly, the compound of Example 1 appears to be converted in vivo to the compound of Example 2, which mediates the observed activity of the compound of Example 1. The compound of Example 1 may have preferable biological absorption when administered orally, and so may be useful as a prodrug.

A number of embodiments of the present invention have been described herein. Nevertheless, it will be understood that various modifications may be made without departing from the scope of the invention as set out in the following claims.

What is claimed is:

1. A method for reducing the severity of convulsant activity, comprising administering to a subject a therapeutically effective amount of a compound of formula (I):

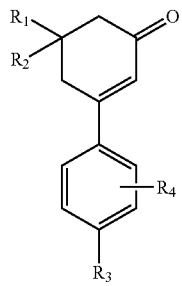

wherein,
$R_1=R_2=CH_3$ or $R_1=H$ and $R_2=H$;
$R_3=H$;
F;
$C(O)R_5$, wherein $R_5=H$, $CH_3$, $C_2H_5$, $CH(CH_3)_2$, $CHCH_3CN$, or aryl, wherein aryl is a compound selected from the group consisting of:
  phenyl, unsubstituted or substituted with one or two compounds selected from the group consisting of $CH_3$, OH, $OCH_3$, $SO_2CH_3$, $SO_2Ph$, F, Cl, $CF_3$, CN;
  1- or 2-naphthyl;
  2-, 3-, or 4-pyridyl, unsubstituted or substituted with one or two compounds selected from the group consisting of $CH_3$, $OCH_3$, $SO_2CH_3$, $SO_2Ph$, F, Cl, $CF_3$, CN;
  2- or 3-furyl, unsubstituted or substituted with one or two compounds selected from the group consisting of $CH_3$, $OCH_3$, $SO_2CH_3$, $SO_2Ph$, F, Cl, $CF_3$, CN; and
  2- or 3-thienyl, unsubstituted or substituted with one or two compounds selected from the group consisting of $CH_3$, $OCH_3$, $SO_2CH_3$, $SO_2Ph$, F, Cl, $CF_3$, CN;
$C(O)$—$O^-$, or $C(O)$—$O$—$R_6$, wherein $R_6=H$, straight or branched C1 to C6 alkyl, phenyl, $CH_2C_6H_5$, or $CH(CH_2)n$, and wherein n=2-5;
$C(O)NH_2$, $C(O)NHR_6$ or $C(O)NR_7R_8$ wherein $R_7$ and $R_8$ independently =straight or branched C1 to C6 alkyl, $CH_2C_6H_5$, aryl, or $R_7$ and $R_8$ together =$(CH_2)n$, and wherein n=3-5;
OH, $OCH_3$, O—$C(O)CH_3$ or $OCH_2C_6H_5$;
S—$CH_3$, S—$C_6H_5$, $S(O)CH_3$, $S(O)C_6H_5$, $SO_2CH_3$, or $SO_2C_6H_5$;
$NO_2$, $NH_2$, $NHR_6$, $NR_7R_8$;
C≡C—$C(O)CH_3$, C≡C—$C(O)CH(CH_3)_2$, C≡C—$C(O)C_2H_5$, C≡C—$C(O)C_6H_5$, C≡C—$C(O)$—OH, or C≡C—$C(O)$—$O^-$; or
CN; and
$R_4$=one or two compounds selected from the group consisting of H, $CH_3$, OH, $OCH_3$, $SO_2CH_3$, $SO_2Ph$, F, Cl, $CF_3$, or CN,
or a pharmaceutically acceptable salt thereof,
wherein when $R_1$ and $R_2$ are both H and $R_4$ is OH, then $R_3$ is not OH or $OCH_3$.

2. The method of claim 1, wherein $R_1=R_2=CH_3$.

3. The method of claim 2, wherein $R_3=H$;
$C(O)R_5$, wherein $R_5=H$, $CH_3$, $C_2H_5$, $CH(CH_3)_2$, $CHCH_3CN$, or aryl;
$C(O)$—$O^-$, or $C(O)$—$O$—$R_6$, wherein $R_6=H$, straight or branched C1 to C6 alkyl, $CH_2C_6H_5$, or $CH(CH_2)n$, and wherein n =2-5;

C(O)NH$_2$, C(O)NHR$_6$ or C(O)NR$_7$R$_8$ wherein R$_7$ and R$_8$ independently =straight or branched C1 to C6 alkyl, CH$_2$C$_6$H$_5$, aryl, or R$_7$ and R$_8$ together =(CH$_2$)n, and wherein n =3-5; or OH, OCH$_3$, or OCH$_2$C$_6$H$_5$.

4. The method of claim 1, wherein the compound of formula (I) is:

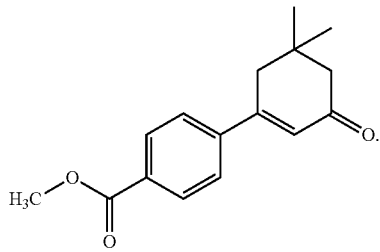 [SMILES: COC(=O)c1ccc(C2=CC(=O)CC(C)(C)C2)cc1]

5. The method of claim 1, wherein the compound of formula (I) is:

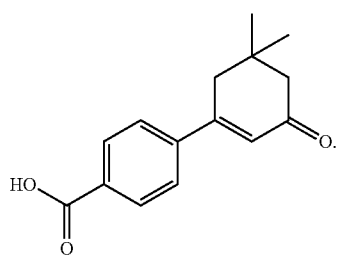 [SMILES: CC1(C)CC(=O)C=C(c2ccc(C(=O)O)cc2)C1]

6. The method of claim 1, wherein the of formula (I) is:

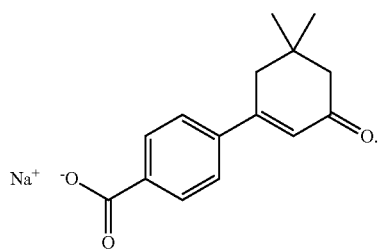

7. The method of claim 1, wherein the compound of formula (I) is:

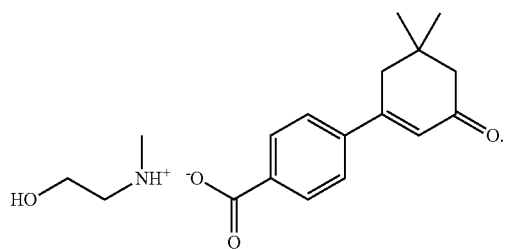

8. The method of claim 1, wherein the compound of formula (I) is:

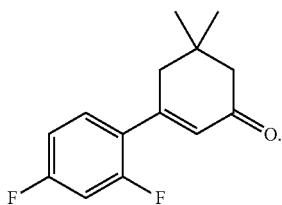 [SMILES: CC1(C)CC(=O)C=C(c2ccc(F)cc2F)C1]

9. The method of claim 1, wherein the compound of formula (I) is:

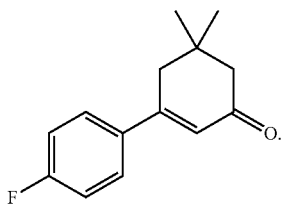 [SMILES: CC1(C)CC(=O)C=C(c2ccc(F)cc2)C1]

10. The method of claim 1, wherein the compound of formula (I) is:

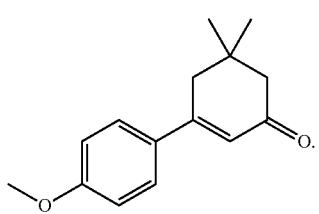 [SMILES: COc1ccc(C2=CC(=O)CC(C)(C)C2)cc1]

11. The method of claim 1, wherein the compound of formula (I) is:

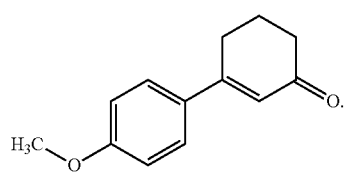

12. The method of claim 1, wherein the compound of formula (I) is:

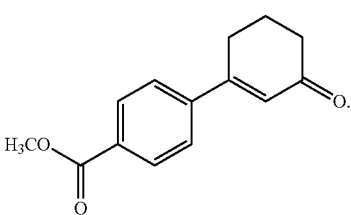

13. The method of claim 1, wherein the compound of formula (I) is:

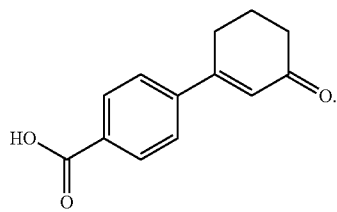 [SMILES: O=C1C=C(c2ccc(C(=O)O)cc2)CCC1]

14. The method of claim 1, wherein the compound of formula (I) is:

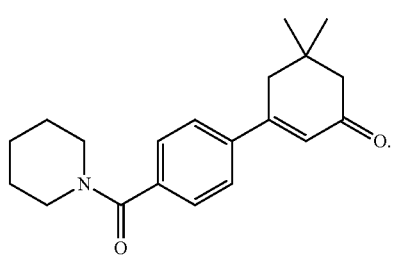 [SMILES: CC1(C)CC(=O)C=C(c2ccc(C(=O)N3CCCCC3)cc2)C1]

15. The method of claim 1, wherein the compound of formula (I) is:

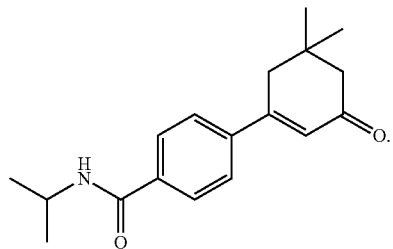 [SMILES: CC(C)NC(=O)c1ccc(C2=CC(=O)CC(C)(C)C2)cc1]

16. The method of claim 1, wherein the compound of formula (I) is:

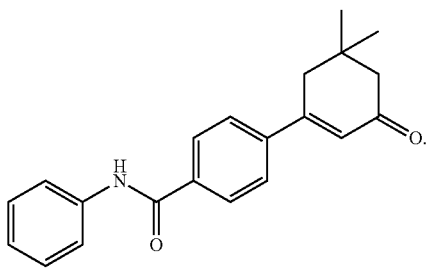 [SMILES: CC1(C)CC(=O)C=C(c2ccc(C(=O)Nc3ccccc3)cc2)C1]

17. The method of claim 1, wherein the compound of formula (I) is:

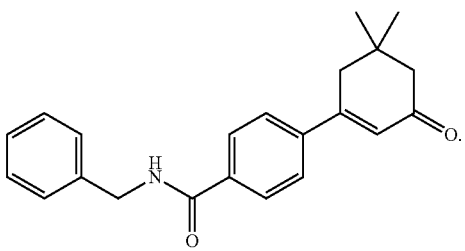 [SMILES: CC1(C)CC(=O)C=C(c2ccc(C(=O)NCc3ccccc3)cc2)C1]

18. The method of claim 1, wherein the compound of formula (I) is:

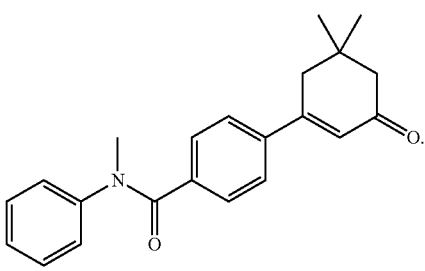 [SMILES: CN(C(=O)c1ccc(C2=CC(=O)CC(C)(C)C2)cc1)c1ccccc1]

19. The method of claim 1, wherein the compound of formula (I) is:

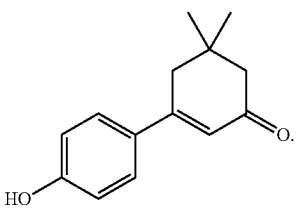 [SMILES: CC1(C)CC(=O)C=C(c2ccc(O)cc2)C1]

20. The method of claim 1, wherein the compound of formula (I) is:

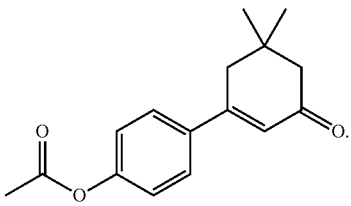 [SMILES: CC(=O)Oc1ccc(C2=CC(=O)CC(C)(C)C2)cc1]

* * * * *